United States Patent [19]

Sjöquist et al.

[11] 3,966,898

[45] June 29, 1976

[54] METHOD AND REAGENT FOR DETERMINING IMMUNOLOGIC MATERIALS

[75] Inventors: John A. Sjöquist; Arne V. Sjödin, both of Uppsala, Sweden

[73] Assignee: Pharmacia Diagnostics AB, Uppsala, Sweden

[22] Filed: June 19, 1974

[21] Appl. No.: 480,915

[30] Foreign Application Priority Data

June 28, 1973 Sweden .............................. 7309096

[52] U.S. Cl. ................................. 424/12; 23/230 B; 252/408; 260/112 B; 424/1.5; 195/103.5 R
[51] Int. Cl.² ................. G01N 21/52; G01N 33/16
[58] Field of Search ..................... 23/230 B, 230 D; 424/12, 1, 1.5; 252/408; 195/103.5 R

[56] References Cited
UNITED STATES PATENTS 3,859,430  1/1975  Parikh .............................. 23/230 B

OTHER PUBLICATIONS

Chemical Abstracts, 66:63789x (1967).
Chemical Abstracts, 68:28088n (1968).
Chemical Abstracts, 69:34242v (1968).

*Primary Examiner*—Morris O. Wolk
*Assistant Examiner*—Sidney Marantz
*Attorney, Agent, or Firm*—Fred Philpitt

[57] ABSTRACT

A method of qualitatively or quantitatively indicating immunoglobulin whose Fab-portion is bound to or is caused to bind to an antigen or a hapten or indicating the antigen or hapten which is bound to or caused to bind to the Fab-portion of the immunoglobulin, the immunoglobulin being labelled — before or after binding to the antigen or hapten — with one or more analytically indicatable atoms or groups by contact with a polypeptide labelled with the analytically indicatable atom or group or atoms or groups, wherein the immunoglobulin belongs to the IgG-class and the polypeptide is one which is obtained from microorganisms and which is able to bind itself to the Fc-portion of said immunoglobulin belonging to the IgG-class. The method utilizes an auxiliary agent for labelling immunoglobulin and a reagent for quantitatively or qualitatively indicating antigens or haptens.

3 Claims, No Drawings

METHOD AND REAGENT FOR DETERMINING IMMUNOLOGIC MATERIALS

The present invention relates to a method of qualitatively or quantitatively detecting immunoglobulins whose Fab-portion is bound to or is caused to bind to an antigen or a hapten or detecting the antigen or hapten which is bound to or is caused to bind to the Fab-portion of the immunoglobulin, the immunoglobulin being labelled — before or after binding to the antigen to hapten — with one or more analytically indicatable atoms or groups by contact with a polypeptide labelled with the analytically indicatable atom or atoms or group or groups. The phrase "polypeptide" as used here and in the claims also includes proteins.

Such a method is previously known. Thus, it is previously known to use as a labelled polypeptide an antibody which is labelled with, e.g., radioactive iodine. The preparation of antibodies is a complicated process. Furthermore, antibodies are a heterogeneous material with varying binding ability. If an antibody is prepared against an immunoglobulin, e.g. if antibodies are prepared in a goat against rabbit immunoglobulin, such antibodies will only bind to immunoglobulins from rabbits, but will not generally bind to immunoglobulins from other animals.

For each immunoglobulin to be labelled, it is necessary to prepare a special antibody which can react with the immunoglobulin in question. In addition to the above, the labelling of antibodies with indicatable atoms or groups results in most cases in a loss of immunoactivity. An object of the invention is to at least substantially eliminate these disadvantages.

The invention is mainly characterized in that with the method mentioned in the introduction the immunoglobulin belongs to the IgG-class and the polypeptide is one which is obtained from microorganisms and which has the ability to bind to the Fc-portion of said immunoglobulin belonging to the IgG-class.

Polypeptides with the recited properties from microorganisms are relatively easily obtained and can be labelled with the analytically indicatable atoms or groups in good yields. An important advantage afforded by a labelled polypeptide with the aforementioned properties when used for labelling immunoglobulins in accordance with the method of the invention is that it can bind to the Fc-portion of immunoglobulins from different types of animals, whereby the Fab-portion if left free and is accessible for the binding of antigens and haptens. Previous methods of labelling antibodies directed against the Fc-portion of immunoglobulins required the Fc-fragment of the immunoglobulin in question to be prepared in a pure state, which is a difficult process, and the subsequent immunization of animals with these Fc-fragments for each immunoglobulin for each type of animals.

A further advantage afforded by the labelling method is that, as opposed to antibodies, the polypeptide in question is a unitary substance which can bind to the immunoglobulin in question in a well defined manner.

The indicatable atom or group, or atoms or groups, with which the polypeptide has been labelled may be radioactive and/or colouring and/or fluorescent and/or may contain free radicals and/or have an enzymatic acitvity. Methods of labelling polypeptides according to the aforegoing are described exhaustively in literature and may be applied to the polypeptide from microorganisms relevant in the present context. Examples of radioactive isotopes in this context are, e.g. such isotopes of iodine (e.g. $^{125}I$), $^{14}C$ and tritium which are introduced directly into the polypeptide or by substituting the polypeptide with a group containing the isotope in question. An easy way of labelling the polypeptide is to introduce a fluorescent group, e.g. with the aid of fluorescein isothiocyanate. Enzymes (e.g. a peroxidase or, e.g., a hydrolase such as phosphatase) can be bound to polypeptides by means of CNBr or glutaraldehyde. The analytically indicatable atom or group or atoms or groups with which the polypeptide is labelled and with which the immunoglobulin in question is thus also labelled can readily be detected and determined by conventional methods used herefor.

The mentioned polypeptides from microorganisms used may be, for example, so-called protein A from *Staphylococcus aureus* or a fragment of said protein, which fragment is of polypeptide nature and is able to bind at least one immunoglobulin at its Fc-portion. The aforementioned polypeptides, i.e. protein A and fragments thereof derived from *Staphylococcus aureus* can bind immunoglobulins belonging to the IgG-class at their Fc-portion. Other examples of such polypeptides are polypeptides from *Staphylococcus epidermidis* and from other bacteria species.

Labelling of the immunoglobulin with the aid of the labelled polypeptide can be applied to advantage for qualitatively or quantitatively indicating the immunoglobulin or antigen or hapten, which antigen or hapten is bound to or is caused to bind to the Fab-portion of the immunoglobulin with the method according to the invention.

Labelling of the immunoglobulin with the aid of the labelled polypeptide is effected suitably in the presence of a liquid in which the labelled polypeptide is soluble, preferably an aqueous liquid, under conditions with which the polypeptide is bound to the Fc-portion of the immunoglobulin. Thus, the pH is suitably selected, e.g., around the neutral point, such as within the pH range of 5 – 9, e.g. within the range of 6 – 8.

When desired, the labelled immunoglobulin can be purified, e.g. by gel filtration, or specific adsorption when it exists in solution, or by washing when it exists in an undissolved form, e.g. when bound to an insoluble or insolubilized antigen or hapten or when directly or indirectly bound to an insoluble polymer. Any surplus of free, labelled polypeptides can be removed during the purification of the labelled immunoglobulin.

The invention also relates to an auxiliary agent for labelling immunoglobulin in free or bound form with one or more analytically indicatable atoms or groups comprising or containing a polypeptide labelled with the analytically indicatable atom or group or atoms or groups for use with the method according to the invention. The auxiliary agent is characterized in that the polypeptide is obtained from microorganisms and is able to bind itself to the Fc-portion of immunoglobulin belonging to the IgG-class. The auxiliary agent can be used to advantage in the aforementioned labelling method. The auxiliary agent may exist in the form of a solution, preferably an aqueous solution. It may also exist in solid form, e.g. in freeze-dried form, whereby it can be readily brought into solution when used.

The method of the present invention may form an important step in the qualitative or quantitative determination of an immunoglobulin, e.g. in conjunction with immunochemical reactions where the immunoglobulin is bound to an antigen or a hapten, or is caused to bind to an antigen or a hapten.

The labelling method can be used to prepare a reagent for quantitatively or qualitatively indicating antigens or haptens in free or bound form for use with the method according to the invention. Such a reagent may comprise or contain a reaction product between a polypeptide labelled with one or more analytically indicatable atoms or groups and an immunoglobulin. According to the invention the reagent is characterized in that the polypeptide is obtained from microorganisms and is able to bind to the Fc-portion of immunoglobulins belonging to the IgG-class, so that the antibody-active Fab-portion of the immunoglobulin can bind antigens or haptens.

The reagent may exist in the form of a solution, preferably an aqueous solution. It may also be in solid form, e.g. in freeze-dried form, whereby it can be readily brought into solution when used. The reagent is suitably used in the presence of a liquid, preferably an aqueous liquid, under such conditions that the antibody-active Fab-portion of the immunoglobulin can bind to antigens or haptens. The antigen or hapten may be in free or bound form, e.g. bound to a cell surface or to a polymer, e.g. an insoluble polymer. The antigen may also be bound to another antibody.

The invention will now be illustrated by means of a number of examples.

EXAMPLE 1

The preparation of labelled protein A from S. aureus

A. The preparation of raw extract of protein A from S. aureus

S. aureus, species Cowan I, was cultured in accordance with the directives given in European J. Biochem. Vol. 29 (1972), page 572 (Sjöquist et al).

Protein A was liberated from the bacteria by means of the enzyme preparation lysostaphin; insoluble material was removed by centrifuging; the liquid phase was recovered; the pH was adjusted to 3.5 with HCl; insoluble material was then removed by centrifuging and the liquid recovered, whereafter the pH was adjusted to 7.0 with NaOH, all in accordance with the aforementioned reference. The liquid obtained comprises a raw extract containing protein A in mixture with substances of a contaminating nature.

B. The preparation of agarose with IgG bound thereto

For this purpose there was used agarose in the form of the commercially available preparation Sepharose 4 B (Pharmacia Fine Chemicals AB, Uppsala, Sweden).

The agarose was used in the form of small particles (40 – 190 micrometers), swollen in water. The particle mass contained 4 % by weight of agarose. The mass was first washed with water. To 100 ml of packed particle mass admixed with 50 ml water were added 10 grams of CNBr in 50 ml of water at 20°C whilst stirring, the pH being maintained at from 10 to 11 by adding 5 normal NaOH. After 10 minutes the particle mass was washed thoroughly with ice cold water and then with a 0.2 M sodium carbonate-sodium hydrogen carbonate buffer in water with pH 9.0 at 4°C.

The particle mass activated with CNBr was slurried in 120 ml of the above mentioned buffer with pH 9.0, containing 3.0 grams of human IgG (obtained from Kabi AB, Stockholm, Sweden) at 4°C whilst stirring.

After 4 hours the particle mass was removed by filtration and washed with the aforementioned buffer with pH 9.0 and was then suspended in 1.5 liters of an aqueous solution containing 0.05 M 2-amino-ethanol and 0.2 M sodium carbonate-sodium hydrogen carbonate with pH 9.0 and was stirred for 18 hours at 4°C. The particle mass was then washed with a 0.1 M sodium phosphate buffer in water containing 4 M urea with pH 6.0 and then with a 0.1 M sodium phosphate buffer in water with pH 7.0, until the OD 280 nanometers of the washing liquid was less than 0.01. The gel mass was then washed with a 0.1 M glycine-HCl buffer in water with pH 3.0, and was then washed again with the aforementioned 0.1 M sodium phosphate buffer with pH 7.0. The obtained product contained approx. 30 milligrams of bound IgG per 1 ml packed particle mass.

C. The separation of protein A from raw extract from S. aureus

A chromatography column was filled with 100 ml of the packed particle mass having IgG bound thereto and a pH 7.0 from step B above. 500 ml of the raw extract with pH 7.0 and containing protein A from step A above was caused to pass slowly through the column containing the particle mass at 20°C, the rate of flow through the column being adjusted to 50 ml per hour. The particle mass of the column was then carefully washed with 0.1 M sodium phosphate buffer in water with pH 7.0, until the OD 280 nanometers of the washing liquid was less than 0.02. The obtained product contained approximately 3 milligrams of bound protein A per 1 ml of packed particle mass.

D. The separation of protein A from the particle mass

Protein A bound to the particle mass obtained from step C above was released from said mass by eluting the column at an acid pH, e.g. with 100 ml of 0.1 M glycine-HCl buffer in water with a pH of 3.0. The collected glycine-HCl buffer containing protein A was dialyzed against distilled water, whereafter protein A was obtained in solid form by freeze drying. Approximately 250 milligrams of protein A were obtained in pure form. (Alternatively, de-salting may be effected by means of gel filtration instead of dialysis.) By means of immunological tests etc., it was established that the protein A contained no substances of a contaminating nature.

E. The preparation of labelled protein A

Protein A obtained according to the above was labelled with $^{125}I$ according to a method based on the use of iodine monochloride as a reagent. Labelling can be effected in accordance with the following:

Radioactive iodine ($^{125}I$)

Iodine-125, carrier free and dissolved as NaI in 0.1 M NaOH and free from reducing agent was used.

Iodine monochloride

Iodine monochloride was prepared according to J. L. Izzo, W. F. Bale, M. J. Izzo and A. Roncone, J. Biol. Chem. 239, No. 11 (1964) 3742 and the iodine content was determined by the reduction of all iodine to iodide with arsenic trioxide and subsequent titration with 0.1 M $AgNO_3$. The stock solution of ICl contained 2.54 mg I/ml in 0.02 M KCl, 2.0 M NaCl and 1.0 M HCl and is stable at room temperature for at least 18 months. Prior to being used, the basic solution of ICl was diluted to the necessary concentration. The diluent used was an HCl-NaCl-solution, the concentration of which was adjusted individually for each experiment, so as to be well above the minimum concentrations of HCl and NaCl at which ICl is known to be stable (R. W. Helmkamp, M. A. Contreras and W. F. Bale: Int. J. Appl. Radiat. Isotopes, 18 (1967) 737).

Labelling process

The iodination was based on Helmkamp's modification of McFairlane's iodine monochloride method (A. S. McFairlane, Nature, 182 (1958) 53) with additional modifications (J. L. Izzo, W. F. Bale, M. J. Izzo and A. Roncone, J. Biol. Chem. 239, No. 11 (1964) 3743, W. F. Bale, R. W. Helmkamp, T. P. Davis, M. J. Izzo, R. L. Cooland, M. A. Contreras and J. L. Spar, Proc. Soc. Exp. Med., 122 (1966) 407 and R. W. Helmkamp, M. A. Contreras and W. F. Bale, Int. J. Appl. Radiat. Isotopes, 18 (1967) 737). Protein A (100 μg) was labelled with a molar ratio of ICl to protein A of 1.875:1 and ICl to $^{125}$I of 2:1. The following solutions were used:

SOLUTION I: Protein A was dissolved in 0.05 M sodium phosphate buffer, pH 7.4, to a concentration of 5 mg/ml.

SOLUTION II: The diluent (0.12 M HCl, 1.0 M NaCl) for the stock ICl solution was prepared by dissolving 5.84 g NaCl in 12 ml of 1.0 M HCl and 50 ml of distilled water, whereafter further distilled water was added to obtain a final volume of 100 ml.

SOLUTION III: The final iodine monochloride solution was prepared by diluting 100 μl of the stock ICl solution with 15.58 g of solution II.

SOLUTION IV: 19.4 μl of the radioiodide (5.9 mCi) were added to 40 μl of solution III and placed in an ice bath prior to being used.

All solutions were kept cold and the iodination reaction was carried out at 0°C. The reagents were added in the following order, in a small glass tube: 50 μl of solution IV were added, to 70 μl sodium borate and carbonate buffer (0.24 M with respect to borate and 0.16 M with respect to carbonate, pH 9.1 ) and 20 μl of solution I (100 μg protein A) and immediately thoroughly mixed. After 120 seconds, 20 μl of 0.01 M $Na_2S_2O_3$, 50 μl 2 % KI and 200 μl 3 % aqueous solution of dextran having an average molecular weight of $\overline{M}_w =$ 20,000 were added to the mix. $^{125}$I-iodinated protein A preparation can be purified by gel filtration using dextran cross-linked with epichlorohydrin in alkaline solution (Sephadex or polyacrylamide), or by dialysis. Fractions from the gel filtration column were recovered at around +4°C in 0.05 M sodium phosphate buffer, pH 7.4, containing 0.05 % Tween 20 (polyethylene glycol 900 — sorbitanmonolaurate) and 3 % dextran having an average molecular weight of $\overline{M}_w = 20,000$. The fractions in which labelled protein A were indicated were combined and stored in a frozen state.

This method gave a yield of approximately 75 % with respect to the theoretically calculated quantity of iodine which could be bound. The labelled protein A contained approximately 0.5 atoms $^{125}$I and about 1 atom $^{127}$I per molecule ($\overline{M}_w$ 42,000) and had a specific activity of approximately 24 mCi/mg.

EXAMPLE 2

The preparation of polypeptide fragments of protein A from S. aureus for labelling purposes.

A. The preparation of raw extract of polypeptide fragments of protein A from S. aureus S. aureus, species Cowan I, were cultivated in accordance with the directives given in European J. Biochem. Vol. 29 (1972), page 572 (Sjöquist et al).

The bacteria were removed by centrifuging and then washed with 0.9 % NaCl solution in water. 100 grams of bacteria (wet weight) were slurried in 150 ml of a physiological common salt solution. To this were added 10 mg of trypsin (free from chymotrypsin). The pH was 7.2. The enzyme treatment was carried out at 30°C and at a pH of 7.2 for 30 minutes, whereafter 20 mg of trypsin-inhibitor from soya beans were added. The suspension was then centrifuged. The supernatant was then recovered and sterilized by filtering the same through Millipore-filter.

The sterile, filtered liquid contained fragments of protein A of a polypeptide character in mixture with substances of a contaminating nature. In order to purify fragments capable of binding to the Fc-portion IgG molecules, said fragments were isolated with the aid of agarose having IgG bound thereto.

B. The preparation of agarose having IgG bound thereto

Agarose with IgG bound thereto was prepared in the same manner as in example 1, part B. The obtained product contained approximately 30 milligrams of bound IgG per 1 ml of packed particle mass.

C. The separation of polypeptide fragments of protein A from S. aureus

A chromatography column was filled with 100 ml of the packed particle mass with IgG bound thereto having a pH 7.0 and obtained from step B above. 100 ml of the raw extract with pH 7.0 containing polypeptide fragments of protein A from step A above was passed slowly through the column containing the particle mass at 20°C, the rate of flow through the column being adjusted to 50 ml per hour. The particle mass in the column was then washed thoroughly with 0.1 M sodium phosphate buffer in water with pH 7.0 until the OD 280 nanometers of the washing liquor was less than 0.02. The obtained product contained approximately 1 milligram of bound polypeptide per 1 ml of packed particle mass.

D. The separation of polypeptide fragments from protein A from the particle mass The polypeptides bound to the particle mass from step C above were liberated from the particle mass by eluting the column at an acid pH, for example with 100 ml of 0.1 M glycine-HCl buffer in water with pH 3.0.

The collected glycine-HCl buffer containing polypeptides capable of binding the Fc-portion of IgG-molecules was de-salted by gel filtration with the aid of Sephadex G 25 (particles of dextran cross-linked with epichlorohydrin). Approximately, 100 mg of polypeptide, which had a molecular weight of approximately 7,000, were isolated by freeze drying. It could be shown by chromatography that the polypeptide fraction comprised several closely related polypeptides, all capable of binding the Fc-portions of IgG molecules. It could be shown by, inter alia, immunological tests that the polypeptide fraction was free from substances of a contaminating nature.

It is possible to isolate in a corresponding manner polypeptide fragments capable of binding the Fc-portion of IgG-molecules, by first isolating protein A in accordance with Pat. No. 3,850,798 (Swedish patent application No. 14329/72) and then treating protein A in solution at, e.g. pH 8.2 with trypsin in an analogous manner as that described above, whereafter the polypeptide fragments having the desired properties are separated in a manner corresponding to that described in example 2, by binding said fragments to agarose with IgG bound thereto and then separating the polypeptide fragments.

The polypeptide products obtained can be used for labelling, e.g. with fluorescent groups or radioactive atoms or groups. Similar to protein A, the obtained polypeptide product can thus be labelled, for example in a conventional manner with the aid of fluoresceinisothiocyanate. The product labelled with the aid of fluoresceinisothiocyanate can be used to advantage for labelling immunoglobulin of the IgG-class. This can be used for qualitatively or quantitatively indicating the immunoglobulin or antigen or hapten which is bound to or caused to bind to the Fab-portion of the immunoglobulin with the method of the present invention.

Labelling with fluoresceinisothiocyanate can be effected, e.g. in the following manner: 10 mg of the polypeptide product dissolved in 1 ml of 0.25 M aqueous solution of sodium carbonate-sodium hydrogen carbonate buffer with pH 9, said solution also containing 0.45 % NaCl, may be added with 1 mg of fluoresceinisothiocyanate, whereafter the mixture may be agitated for some minutes and allowed to stand at 4°C for 12 hours. The mixture is then centrifuged. To cleanse the solution with the labelled polypeptide from unreacted fluoresceinisothiocyanate, the mix may be gel filtered in a column filled with gel particles comprising dextran cross-linked with epichlorohydrin (Sephadex G 25) swollen in 0.9 percent aqueous solution of NaCl and eluted with the same solution. The eluted fraction with labelled polypeptide is then recovered. The pH is adjusted to 7. The solution is stored in a frozen state and the product may be freeze dried. The product is fluorescent in ultraviolet light. Analogously labelling can be carried out with, e.g. tetramethylrhodamineisothiocyanate. The labelled polypeptide can bind to the Fc-portion IgG-molecules and can be used with the method of the present invention. This could be proven, e.g. by treating cells on which were seated antibodies of the IgG class, immunochemically bound to cell surface antigens, with the aid of a solution of protein A labelled with the aid of fluoresceinisothiocyanate in phosphate buffer with pH 7.2. Subsequent to washing the cells with the same buffer, the fluorescence from the labelled protein A, which was bound to the antigen-bound IgG on the cell surfaces, could be detected and measured.

EXAMPLE 3

The indication of antigen-bound immunoglobulin of the IgG-class with the aid of labelled protein A For this test there was used $^{125}$I-labelled protein A from example 1 above, to indicate rabbit IgG-antibodies against human IgE, the IgG-antibodies being immunochemically bound by means of their Fab-portions to human IgE (the antigen), which in turn was covalently bound by means of cyanogen bromide to small particles of dextran cross-linked in alkaline solution with epichlorohydrin (Sephadex G 25, ultrafine).

During the test, 0.05 mg of said particles having IgE bound thereto were suspended in 1 ml of a physiological common salt solution. The solution was then incubated for 3 hours with 100 µl physiological common salt solution containing 75 nanograms of rabbit anti-IgE-antibodies. The particles were then washed three times, each time with 2.5 ml of physiological common salt solution, with the aid of centrifuging.

100 µl of physiological common salt solution containing 2 nanograms of $^{125}$I-labelled protein A were then added and the mixture incubated for 18 hours and then washed 5 times, each time with 2.5 ml physiological common salt solution and with centrifuging. The gamma radiation (Wallac gamma-counter) of the particle material was then measured. Approximately 25,000 counts per 5 minutes were obtained compared with a blank which showed that IgG-antibodies which had linked to the antigen (IgE) were present on the particles.

EXAMPLE 4

The indication of IgE (antigen) with the aid of labelled protein A bound to antibodies against IgE $^{125}$I labelled protein A (from example 1 above) bound to the Fc-portion of antibodies (belonging to the IgG-class) against IgE was used for the test. The reagent was obtained by incubating for 2 hours 40 nanograms of $^{125}$I-labelled protein A and 100 nanograms of rabbit-anti-IgE in 2 ml of physiological common salt solution. (There was a surplus of labelled protein A).

0.05 mg of Sephadex particles G-25 ultrafine (i.e. dextran cross-linked with epichlorohydrin) with human IgE (antigen) bound thereto by means of cyanogen bromide were suspended in 1 ml of a physiological common salt solution. 100 µl of the reagent solution according to the above were then added. After 18 hours the particles were washed by centrifuging the same five times with 2.5 ml of a physiological common salt solution. The gamma radiation (Wallac gamma-counter) of the particle material was then measured. 40,000 counts per 2 minutes were obtained compared with a blank, which shows that IgE (the antigen) was present on the particles.

EXAMPLE 5

Protein A labelled with peroxidase

Peroxidase was coupled to protein A from *S. aureus* from example 1 in the following manner: 15 mg of peroxidase (from horse-radish, Sigma) were dissolved in 0.2 ml of a 1.25 percent solution of glutaraldehyd in a 0.1 M aqueous solution of sodium phosphate with pH 6.8. The solution was allowed to stand at 20°C for 18 hours. The solution was then passed through a column (length 50 cm, diameter 1 cm) filled with swollen particles of dextran cross-linked with epichlorohydrin (Sephadex G-25, Pharmacia Fine Chemicals AB, Uppsala, Sweden) and a 0.1 M aqueous solution of sodium phosphate (pH 6.8). The same phosphate buffer was used for eluting the column. The coloured fractions which were eluted in the void volume were recovered during this gel chromatography. The collected coloured fractions were concentrated to 1 ml by ultra-filtration (PM-10 membrane, retains proteins having a molecular weight of over 10,000). 5 mg of protein A dissolved in 1 ml of the aforementioned phosphate buffer were added to the glutaraldehyd activated solution (1 ml) of peroxidase. Thereafter there were added 0.2 ml of a 1 M sodium carbonate-sodium hydrogen carbonate buffer (in water) with pH 9.5. The mixture was allowed to stand at 4°C for 24 hours. 0.2 ml of a 0.2 M aqueous solution of lysine were then added. (The pH of the lysine solution had been adjusted to 7.0 with a 5 M aqueous solution of NaOH). After adding the lysine, the mixture was allowed to stand at 20°C for 2 hours. The solution was then passed through a column (length 10 cm, diameter 1 cm) filled with swollen IgG agarose particles and 0.1 M aqueous solution of sodium phosphate with pH 6.8. (The IgG agarose was prepared in a similar manner as in example 1). Protein A with peroxidase coupled thereto adhered to the IgG on the agarose particles. 0.1 M aqueous solution of sodium phosphate with pH 6.8 was passed through the column, to wash away non-bound substances. The column was then eluted with a 0.1 M glycine-HCl buffer (in water) with pH 3.0. The coloured fractions were recovered and combined. The solution was neutralized with 5 M of an aqueous NaOH solution. The solution was concentrated to 1 ml by ultra-filtration (UM-2 membrane, retains substances having a molecular weight over approximately 2,000). The solution was dialyzed for 12 hours against a buffer with pH 7.2. (The buffer was prepared by dissolving in water 8.0 g NaCl, 0.2 g KCl, 1.15 g $Na_2HPO_4$ and 0.2 g $KH_2PO_4$ per liter of solution.) The protein A solution labelled with peroxidase can be sterilized by filtering the same through a Millipore-filter. The solution is suitably stored at 4°C.

Protein A having peroxidase bound thereto can be used with the method according to the invention, the peroxidase activity being determined in a conventional manner. Analogously with Example 2, it was possible to show that the aforedescribed protein A having peroxidase bound thereto binds to IgG-antibodies (directed against an antigen) which are immunochemically bound to antigens seated on cell surfaces, by detection of the peroxidase. In this way, the antigen bound immunoglobulin IgG could be indicated, while the antigen bound to IgG could also be indicated indirectly by simple enzyme-chemical determination processes.

What is claimed is:

1. In the method of qualitatively or quantitatively indicating an immunoglobulin belonging to the IgG-class, the Fab-portion of which immunoglobulin is bound to an antigen or hapten, the immunoglobulin being labelled, before or after binding to the antigen or hapten, with one or more analytically indicatable atoms or groups by contacting said immunoglobulin with a polypeptide labelled with said analytically indicatable atoms or groups, the improvement which comprises using as the polypeptide, a polypeptide which is obtained from Staphylococci and which is able to bind itself to the Fc-portion of said immunoglobulin belonging to the IgG-class.

2. A method as set forth in claim 1, wherein the indication of the immunoglobulin belonging to the IgG-class is used for the indication of an antigen or a hapten which is bound to the Fab-portion of said immunoglobulin.

3. A reagent for quantitatively or qualitatively indicating antigens or haptens in free or bound form, which reagent comprises a reaction product between (a) an immunoglobulin belonging to the IgG-class and having a Fab-portion which has an antibody activity against an antigen or a hapten and (b) a polypeptide which is obtained from Staphylococci and subsequently labelled and which is able to bind to the Fc-portion of said immunoglobulin belonging to the IgG-class, the polypeptide being bound to the Fc-portion of the immunoglobulin leaving the antibody active Fab-portion of the immunoglobulin free to bind antigen or hapten.

* * * * *